(12) United States Patent
Shimizu et al.

(10) Patent No.: US 10,471,232 B2
(45) Date of Patent: Nov. 12, 2019

(54) CATHETER AND BALLOON CATHETER (71) Applicant: ASAHI INTECC CO., LTD., Seto-shi, Aichi (JP)

(72) Inventors: Yuusuke Shimizu, Owariasahi (JP); Hiroshi Ito, Miyohshi (JP); Shogo Hase, Sakura (JP)

(73) Assignee: ASAHI INTECC CO., LTD., Seto-shi (JP)

( * ) Notice: Subject to any disclaimer, the term of this patent is extended or adjusted under 35 U.S.C. 154(b) by 71 days.

(21) Appl. No.: 15/605,047

(22) Filed: May 25, 2017

(65) Prior Publication Data
US 2018/0093073 A1 Apr. 5, 2018

Related U.S. Application Data (63) Continuation of application No. PCT/JP2016/079471, filed on Oct. 4, 2016.

(51) Int. Cl.
*A61M 31/00* (2006.01)
*A61M 37/00* (2006.01)
(Continued)

(52) U.S. Cl.
CPC ...... *A61M 25/0052* (2013.01); *A61M 25/001* (2013.01); *A61M 25/005* (2013.01); *A61M 25/0108* (2013.01); *A61M 25/10* (2013.01); *A61M 25/1002* (2013.01); *A61M 25/104* (2013.01); *A61M 2025/0183* (2013.01); *A61M 2025/1045* (2013.01); *A61M 2025/1079* (2013.01)

(58) Field of Classification Search
CPC ...... A61M 2025/1045; A61M 25/0052; A61M 25/0108; A61M 25/1002; A61M 25/10; A61M 25/0045
See application file for complete search history.

(56) References Cited

U.S. PATENT DOCUMENTS 5,863,366 A * 1/1999 Snow ............... A61B 17/12022
156/143
6,648,874 B2 11/2003 Parisi et al.
(Continued)

FOREIGN PATENT DOCUMENTS

EP 1 259 270 B1 3/2006
EP 3 025 750 A1 6/2016
(Continued)

*Primary Examiner* — Rebecca E Eisenberg
(74) *Attorney, Agent, or Firm* — Oliff PLC (57) ABSTRACT

A catheter includes a tubular inner layer, a reinforcing layer disposed at least partially within the inner layer or on an outer circumference of the inner layer, and an outer layer. The reinforcing member is made of wound wires, each adjacent pair of the wires having a gap therebetween. A bonding portion is disposed in the gap of the reinforcing layer and includes an inner layer protruding portion of the inner layer that extends into the outer layer and is engaged with an outer layer protruding portion of the outer layer that extends into the inner layer. This configuration enlarges the area across which the outer layer and the inner layer are bonded to each other within the gap of the reinforcing layer, leading to a strengthened bond between the outer layer and the inner layer.

6 Claims, 12 Drawing Sheets (51) Int. Cl.
*A61M 25/00* (2006.01)
*A61M 25/01* (2006.01)
*A61M 25/10* (2013.01)

(56) References Cited

U.S. PATENT DOCUMENTS

| | | | |
|---|---|---|---|
| 2010/0030165 A1* | 2/2010 | Takagi | A61L 29/085 604/265 |
| 2010/0204771 A1* | 8/2010 | Olson | A61F 2/856 623/1.11 |
| 2011/0087191 A1* | 4/2011 | Scheuermann | A61L 29/16 604/509 |
| 2014/0083969 A1* | 3/2014 | Porter | A61M 25/0012 216/7 |
| 2016/0136387 A1 | 5/2016 | Otake et al. | |
| 2018/0078743 A1* | 3/2018 | Kubo | A61M 25/005 |
| 2018/0207683 A1* | 7/2018 | De Wijs | H01L 41/0475 |

FOREIGN PATENT DOCUMENTS

| | | |
|---|---|---|
| JP | 4741151 B2 | 5/2011 |
| JP | 2013-005823 A | 1/2013 |
| JP | 2014-236863 A | 12/2014 |
| JP | 2015-147080 A | 8/2015 |
| WO | 2015/012185 A1 | 1/2015 |
| WO | 2015/099935 A1 | 7/2015 |

* cited by examiner

CATHETER AND BALLOON CATHETER

CROSS REFERENCE TO RELATED APPLICATION

This application is a continuation of PCT/JP2016/079471 filed on Oct. 4, 2016, the contents of which are incorporated by reference herein in their entirety.

BACKGROUND

The disclosed embodiments relate to a medical device. Specifically, the disclosed embodiments relate to a catheter and a balloon catheter used for diagnosis or treatment of a stenosis (also known as a stricture or obstruction) in a blood vessel or digestive organ.

A stenosis that is formed within a blood vessel, a bile duct, a pancreatic duct, or the like interrupts the flow of blood, bile (biliary fluid), pancreatic juice, or the like, respectively. A catheter is conventionally used for diagnosis or treatment of a stenosis.

A typical catheter comprises a tubular inner layer, an outer layer covering the outer circumference of the inner layer, and a reinforcing layer arranged between and bonding together the inner layer and the outer layer. In a catheter of this type comprising a reinforcing layer interposed between an inner layer and an outer layer, it is difficult to strengthen the bond between the inner layer and the outer layer.

Techniques have been developed to solve this problem. One of the techniques involves a catheter having a reinforcing layer with a wavy contour, an inner layer having an outer surface that follows the wavy contour of the reinforcing layer, and an outer layer having an inner surface that follows the wavy contour of the reinforcing layer (see Japanese Patent No. 4741151, for example). Another one of the techniques involves a catheter having a protruding portion that is disposed on an inner layer and that protrudes through a gap in a reinforcing layer toward an outer layer, and that extends in the distal direction to stick into the outer layer (see International Publication No. WO2015/012185, for example).

However, in the catheter described in Japanese Patent No. 4741151, the irregularities provided on the outer circumference of the inner layer and on the inner circumference of the outer layer merely have a wavy contour and no other irregularities are provided. In the catheter described in International Publication No. WO2015/012185, the protruding portion disposed on the inner layer extends in only one direction: from the proximal end toward the distal end. Therefore, there has been a problem that the outer layer readily comes off the inner layer when the outer layer is pulled in the distal direction due to the presence of a stenosis. This problem is more likely to occur when the catheter is inserted into a curved duct such as a blood vessel, a bile duct, or a pancreatic duct, in which case the catheter bends and stress is concentrated at the portion where the outer layer and the inner layer are bonded to each other.

SUMMARY

The disclosed embodiments have been devised based on the above circumstances, and an object of the disclosed embodiments is to provide a catheter and a balloon catheter in which an outer layer does not readily come off an inner layer when the outer layer is pulled in the axial direction (in the distal direction and in the proximal direction) or in the radial direction (outwardly).

The above problem is addressed by the structures discussed below.

A catheter according to the disclosed embodiments includes a tubular inner layer, a reinforcing layer disposed within the inner layer or on an outer circumference of the inner layer, and a first outer layer covering the reinforcing layer. The reinforcing layer is made of wound wires, each adjacent pair of the wires having a gap therebetween. At a first bonding portion disposed in a gap in the reinforcing layer, a first inner layer protruding portion of the inner layer extends into the first outer layer and is engaged with a first outer layer protruding portion of the first outer layer that extends into the inner layer.

This configuration enlarges the area across which the first outer layer and the inner layer are bonded to each other within the gap of the reinforcing layer, leading to a strengthened bond between the first outer layer and the inner layer. And the first bonding portion is anchored in the reinforcing layer, which reduces the probability that the first outer layer will come off the inner layer when the catheter bends (in which case the first outer layer will be pulled in the axial direction (in the distal direction and in the proximal direction)). In addition, the engagement between the first inner layer protruding portion and the first outer layer protruding portion at the first bonding portion can reduce the probability that the first outer layer will come off the inner layer when the first outer layer is pulled in the radial direction (outwardly).

The catheter may further comprise a second outer layer covering the outer circumference of the reinforcing layer, the second outer layer being arranged distal to the first outer layer. The second outer layer may be made of a material that is more flexible than a material of which the first outer layer is made. At a second bonding portion in the gap of the reinforcing layer, a second inner layer protruding portion of the inner layer extends into the second outer layer and is engaged with a second outer layer protruding portion of the second outer layer that extends into the inner layer. A degree of engagement at the second bonding portion is higher than a degree of engagement at the first bonding portion (more specifically, the engaging force between the second inner layer protruding portion and the second outer layer protruding portion at the second bonding portion is stronger than the engaging force between the first inner layer protruding portion and the first outer layer protruding portion at the first bonding portion).

When the catheter is inserted into a peripheral section of a blood vessel, a bile duct, a pancreatic duct, or the like (a vessel), the distal side of the catheter bends to a great extent to follow the curve of the vessel, and stress becomes concentrated at the second bonding portion where the second outer layer made of a flexible material is bonded to the inner layer. However, the high degree of engagement between the second inner layer protruding portion and the second outer layer protruding portion at the second bonding portion (more specifically, the strong engaging force between the second inner layer protruding portion and the second outer layer protruding portion), as well as the enlarged area across which the second outer layer and the inner layer are bonded to each other in the gap of the reinforcing layer, strengthens the bond between the second outer layer and the inner layer, which reduces the probability that the second outer layer made of a flexible material will come off the inner layer.

The catheter may be a balloon catheter. In this case, an inner layer protruding portion extends into the balloon at a bonding portion and is engaged with a balloon protruding portion of the balloon that extends into the inner layer. This configuration enlarges the area across which the balloon and the inner layer are bonded to each other within the gap of the reinforcing layer, leading to a strengthened bond between the balloon and the inner layer. And the balloon is anchored in the reinforcing layer, which reduces the probability that the balloon will come off the inner layer when the balloon catheter bends (in which case the balloon will be pulled in the axial direction (in the distal direction and in the proximal direction)). In addition, the engagement between the inner layer protruding portion and the balloon protruding portion at the bonding portion can reduce the probability that the balloon will come off the inner layer when the balloon is expanded radially (outwardly). The engagement between the inner layer protruding portion and the balloon protruding portion can also allow a reduction in the thickness of the balloon while maintaining the strength of the bond between the balloon and the inner layer, facilitating insertion of the balloon catheter into the vessel.

DETAILED DESCRIPTION OF EMBODIMENTS

Figure 1:
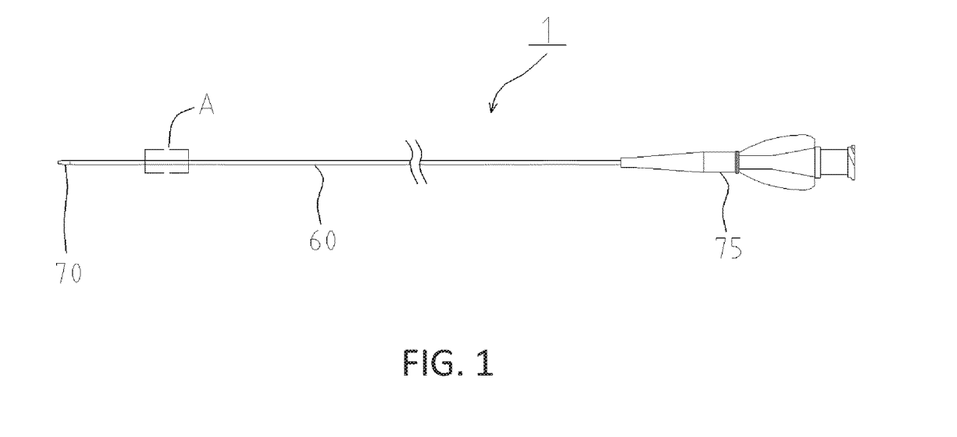
FIG. 1 is an overall view of a catheter according to the disclosed embodiments.
Figure 2:
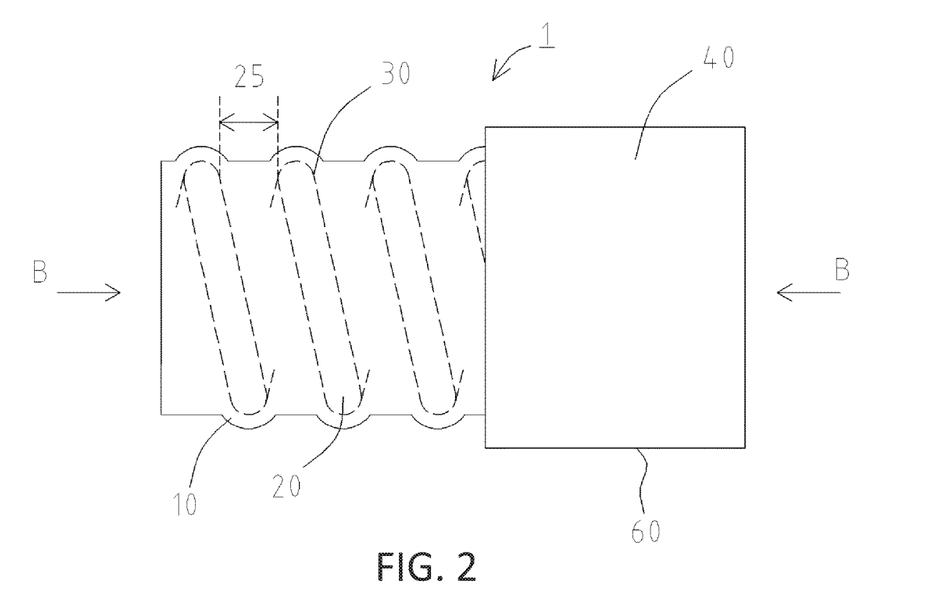
FIG. 2 is an expanded view of part A shown in FIG. 1.
Figure 3:
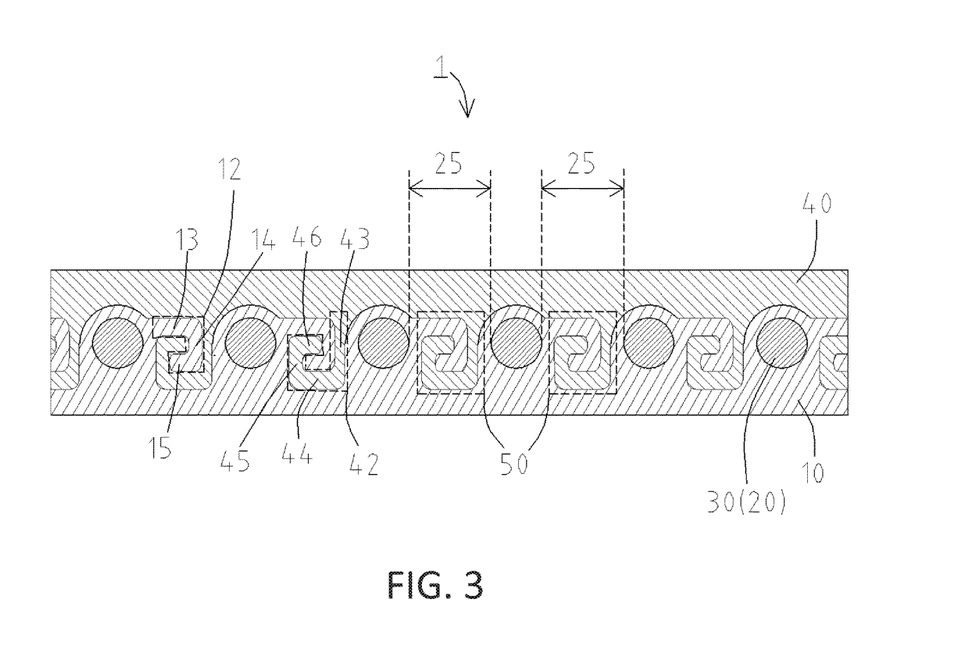
FIG. 3 is a partial sectional view taken along line B-B shown in FIG. 2, showing only the upper side of the catheter.

Referring to FIG. 1 to FIG. 3, a catheter 1 according to the disclosed embodiments is described below. Throughout the figures, the distal end (the front end) to be inserted into the body is shown to the left hand side, and the proximal end (the rear end) to be manipulated by a handler such as a doctor is shown to the right hand side. FIG. 2 is an expanded view of part A shown in FIG. 1. FIG. 3 is a partial sectional view taken along line B-B shown in FIG. 2.

The catheter 1 is, for example, a catheter used for diagnosis or treatment of a stenosis. As shown in FIG. 1, the catheter 1 comprises a catheter shaft 60, a tip 70 bonded to a distal end of the catheter shaft 60, and a connector 75 bonded to a proximal end of the catheter shaft 60.

As shown in FIG. 2, the catheter shaft 60 comprises, in order from inside in the radial direction, a tubular inner layer 10 having a reinforcing layer (coil body) 30 that is disposed therein, and a first outer layer 40 covering the reinforcing layer (coil) 30 and the inner layer 10. The reinforcing layer 30 is made of wound wires 20 with each adjacent pair of the wires 20 having a gap 25 therebetween. For easy understanding, FIG. 2 shows the catheter 1 with the first outer layer 40 partially removed.

The inner layer 10 is made of a resin and can accommodate a guidewire or another catheter inserted thereinto. The resin material constituting the inner layer 10 is not particularly limited, but polytetrafluoroethylene (PTFE) is used for purposes of this discussion.

The coil body as the reinforcing layer 30 is disposed in the tubular inner layer 10. The coil body is made of the wires 20, which are wound in the rightward direction toward the distal end. As the material of the wires 20 constituting the coil body, stainless steel (SUS304) is exemplified. However, the material is not limited to stainless steel. The material may be a different metal material such as tungsten or a Ni—Ti alloy, or a resin material such as reinforced plastic (e.g., polyether ether ketone, or "PEEK"), for example. Alternatively, the wires 20 constituting the coil body may be wound in the leftward direction toward the distal end.

The first outer layer 40 made of a resin is disposed on an outer circumference of the reinforcing layer (coil body) 30 and covers the inner layer 10 and the reinforcing layer (coil body) 30. The resin material constituting the first outer layer 40 is not particularly limited and a polyamide, a polyamide elastomer, a polyester, or a polyurethane, for example, may be used.

Bonded to the distal end of the catheter shaft 60 described above is the tip 70 made of a resin (see FIG. 1). The resin constituting the tip 70 is not particularly limited, and may be a polyurethane or a polyurethane elastomer, for example. The tip 70 may also contain a radiopaque powder. When the tip 70 contains a radiopaque powder (such as a tungsten powder) in a content from about 65 w % to about 90 w %, for example, a handler such as a doctor can keep track of the exact location of the catheter 1 during coronary angiography.

As shown in FIG. 3, disposed in the gap 25 of the reinforcing layer (coil body) 30 is a first bonding portion 50 where a first inner layer protruding portion 12 of the inner layer 10 extends into the first outer layer 40 and is engaged with a first outer layer protruding portion 42 of the first outer layer 40 that extends into the inner layer 10.

The first inner layer protruding portion 12 is composed of a proximally extending portion 13, an inwardly extending portion 14, and a distally extending portion 15 extending from the inner layer 10 in that order. The first outer layer protruding portion 42 is composed of an inwardly extending portion 43, a distally extending portion 44, an outwardly extending portion 45, and a proximally extending portion 46 extending from the first outer layer 40 in that order.

The first bonding portion 50 enlarges the area across which the first outer layer 40 and the inner layer 10 are bonded to each other within the gap 25 of the reinforcing layer (coil body) 30, leading to a strengthened bond between the first outer layer 40 and the inner layer 10. The first bonding portion 50 is anchored in the reinforcing layer (coil body) 30, which the probability that the first outer layer 40 will come off the inner layer 10 when the catheter 1 bends, causing the first outer layer 40 to be pulled in the axial direction (in the distal direction and in the proximal direction). In addition, the engagement between the first inner layer protruding portion 12 and the first outer layer protruding portion 42 can reduce the probability that the first outer layer 40 will come off the inner layer 10 when the first outer layer 40 is pulled in the radial direction (outwardly).

Figure 4:
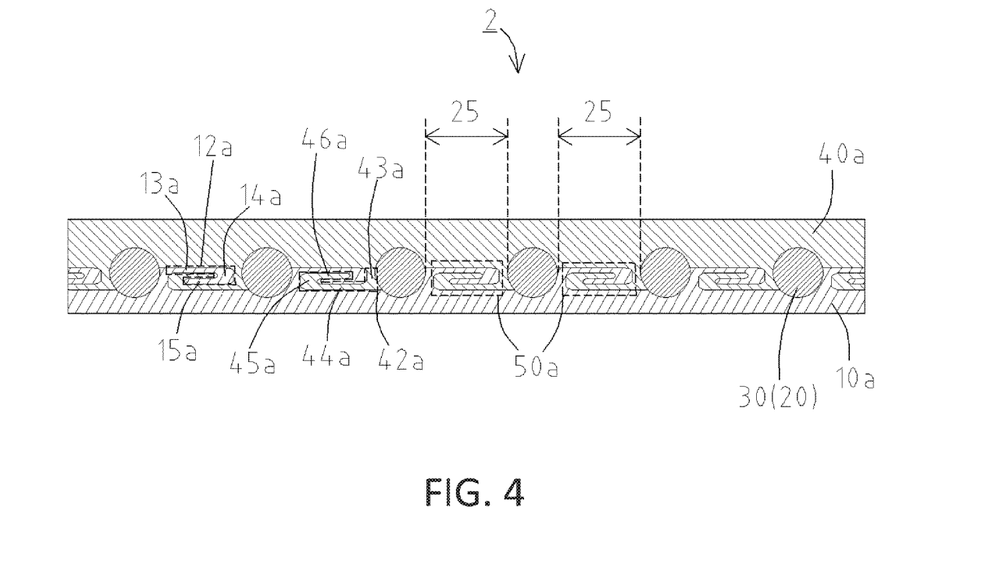
FIG. 4 is a partial sectional view of a catheter according to the disclosed embodiments, viewed in the same manner as in FIG. 3.

Referring to FIG. 4, a catheter 2 according to the disclosed embodiments is described below. Only differences from the catheter 1 shown in FIG. 3 are described below. In the catheter 2, an inward surface of the coil body as the reinforcing layer 30 is buried in an inner layer 10a, and an outward surface of the coil body as the reinforcing layer 30 is buried in a first outer layer 40a. Disposed in the gap 25 of the reinforcing layer (coil body) 30 is a first bonding portion 50a where a first inner layer protruding portion 12a of the inner layer 10a extends into the first outer layer 40a and is engaged with a first outer layer protruding portion 42a of the first outer layer 40a that extends into the inner layer 10a.

The first inner layer protruding portion 12a is composed of a proximally extending portion 13a, an inwardly extending portion 14a, and a distally extending portion 15a. The first outer layer protruding portion 42a is composed of an inwardly extending portion 43a, a distally extending portion 44a, an outwardly extending portion 45a, and a proximally extending portion 46a.

The first bonding portion 50a enlarges the area across which the first outer layer 40a and the inner layer 10a are bonded to each other within the gap 25 of the reinforcing layer (coil body) 30, leading to a strengthened bond between the first outer layer 40a and the inner layer 10a. The first bonding portion 50a is anchored in the reinforcing layer (coil body) 30, which reduces the probability that the first outer layer 40a will come off the inner layer 10a when the catheter 2 bends, causing the first outer layer 40a to be pulled in the axial direction (in the distal direction and in the proximal direction). In addition, the engagement between the first inner layer protruding portion 12a and the first outer layer protruding portion 42a can reduce the probability that the first outer layer 40a will come off the inner layer 10a when the first outer layer 40a is pulled in the radial direction (outwardly).

Figure 5:
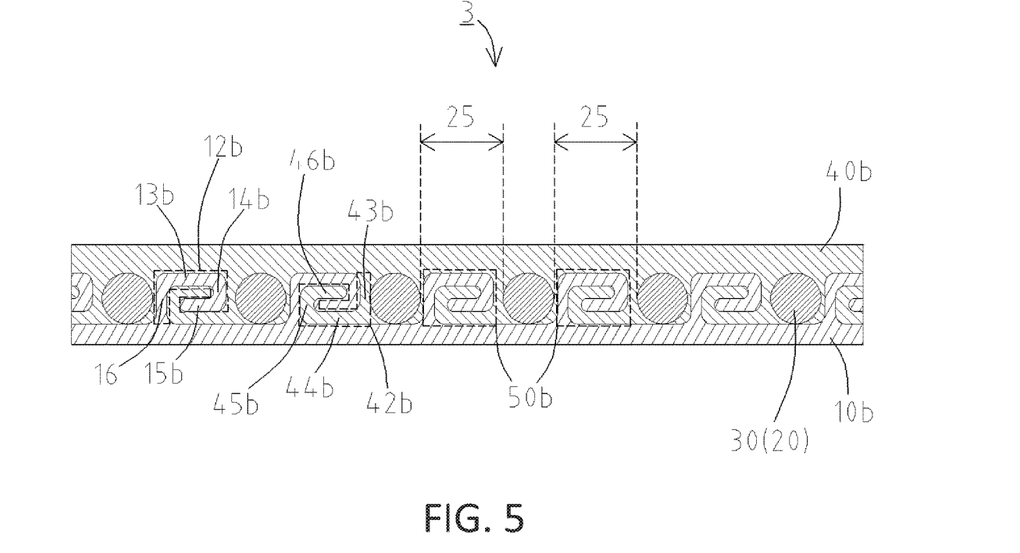
FIG. 5 is a partial sectional view of a catheter according to the disclosed embodiments, viewed in the same manner as in FIG. 3.

Next, referring to FIG. 5, a catheter 3 according to the disclosed embodiments is described below. Only differences from the catheter 1 shown in FIG. 3 are described below. In the catheter 3, the coil body as the reinforcing layer 30 is disposed on an outer circumference of an inner layer 10b. Disposed in the gap 25 of the reinforcing layer (coil body) 30 is a first bonding portion 50b where a first inner layer protruding portion 12b of the inner layer 10b extends into a first outer layer 40b and is engaged with a first outer layer protruding portion 42b of the first outer layer 40b that extends into the inner layer 10b.

The first inner layer protruding portion 12b is composed of an outwardly extending portion 16, a proximally extending portion 13b, an inwardly extending portion 14b, and a distally extending portion 15b. The first outer layer protruding portion 42b is composed of an inwardly extending portion 43b, a distally extending portion 44b, an outwardly extending portion 45b, and a proximally extending portion 46b.

The first bonding portion 50b enlarges the area across which the first outer layer 40b and the inner layer 10b are bonded to each other within the gap 25 of the reinforcing layer (coil body) 30, leading to a strengthened bond between the first outer layer 40b and the inner layer 10b. The first bonding portion 50b is anchored in the reinforcing layer (coil body) 30, which reduces the probability that the first outer layer 40b will come off the inner layer 10b when the catheter 3 bends, causing the first outer layer 40b to be pulled in the axial direction (in the distal direction and in the proximal direction). In addition, the engagement between the first inner layer protruding portion 12b and the first outer layer protruding portion 42b can reduce the probability that the first outer layer 40b will come off the inner layer 10b when the first outer layer 40b is pulled in the radial direction (outwardly).

Figure 6:
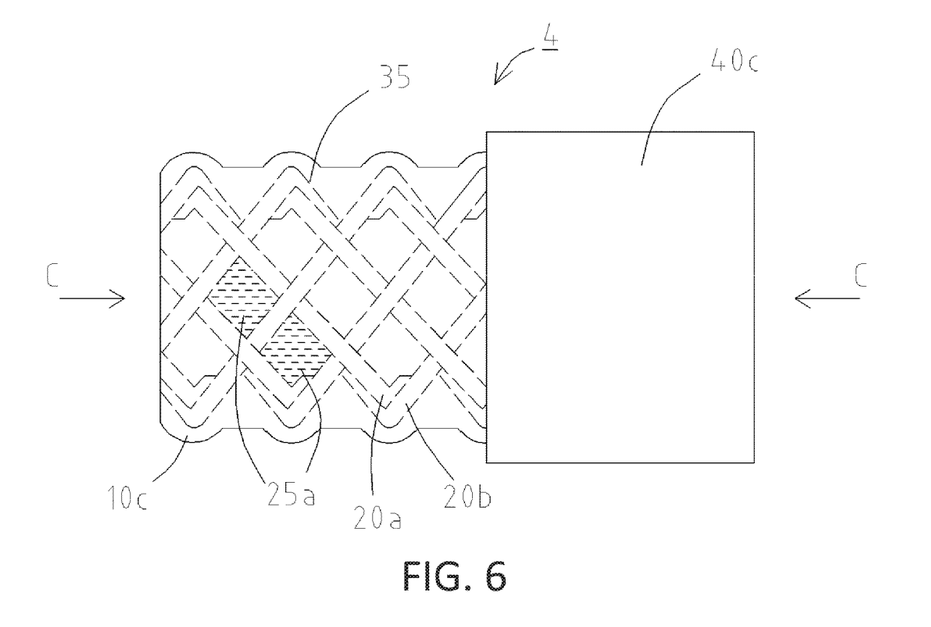
FIG. 6 is an expanded view of a catheter according to the disclosed embodiments, viewed in the same manner as in FIG. 2.

Next, referring to FIG. 6 and FIG. 7, a catheter 4 according to the disclosed embodiments is described below. Only differences from the catheter 1 shown in FIG. 2 will be described. The catheter 4 comprises, in order from inside in the radial direction, an inner layer 10c having a reinforcing layer (braid) 35 disposed therein, and an outer layer 40c covering the reinforcing layer (braid) 35 (see FIG. 6). The reinforcing layer 35 is braided with a plurality of first wires 20a and a plurality of second wires 20b, with each adjacent pair of the first wires 20a and each adjacent pair of the second wires 20b having a gap 25a therebetween. For easy understanding, FIG. 6 shows the catheter 4 with the outer layer 40c partially removed.

The reinforcing layer (braid) 35 is a net (mesh) braided with the first wires 20a and the second wire 20b. The first wires 20a are wound in the rightward direction toward the distal end, and the second wires 20b are wound in the leftward direction toward the distal end. In the catheter 4, eight first wires 20a and eight second wires 20b (i.e., 16 (=8×8) wires in total) are braided, over and under each other to form the reinforcing layer (braid) 35.

The first wires 20a and the second wires 20b constituting the reinforcing layer (braid) 35 may be made of the same material or different materials. The first wires 20a may be made of tungsten, and the second wires 20b may be made of stainless steel (SUS304), for example. Instead of a metal material, a resin material (reinforced plastic, for example) may be used.

Figure 7:
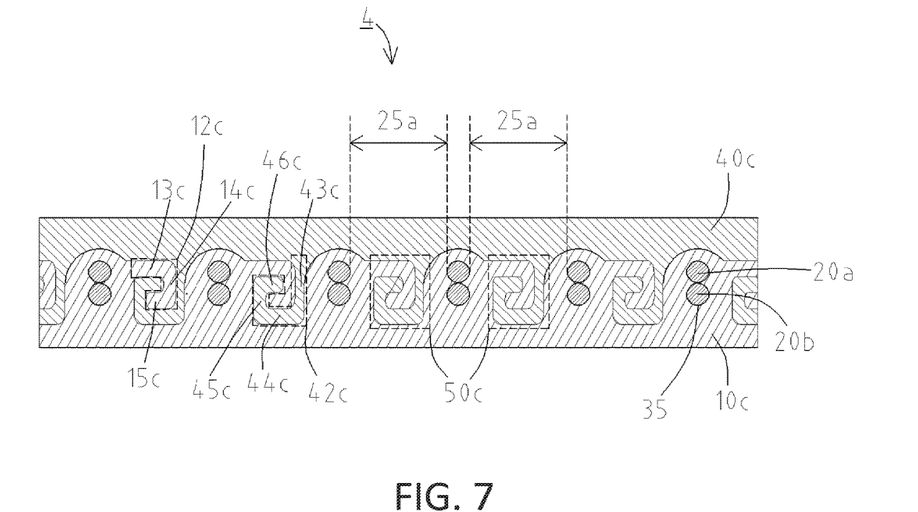
FIG. 7 is a partial sectional view taken along line C-C shown in FIG. 6, showing only the upper side of the catheter.

As shown in FIG. 7, disposed in the gap 25a of the reinforcing layer (braid) 35 is a first bonding portion 50c where a first inner layer protruding portion 12c of the inner layer 10c extends into a first outer layer 40c and is engaged with a first outer layer protruding portion 42c of the first outer layer 40c that extends into the inner layer 10c.

The first inner layer protruding portion 12c is composed of a proximally extending portion 13c, an inwardly extending portion 14c, and a distally extending portion 15c. The first outer layer protruding portion 42c is composed of an inwardly extending portion 43c, a distally extending portion 44c, an outwardly extending portion 45c, and a proximally extending portion 46c.

The first bonding portion 50c enlarges the area across which the first outer layer 40c and the inner layer 10c are bonded to each other within the gap 25a of the reinforcing layer (braid) 35, leading to a strengthened bond between the first outer layer 40c and the inner layer 10c. The first bonding portion 50c is anchored in the reinforcing layer (braid) 35, which reduces the probability that the first outer layer 40c will come off the inner layer 10c when the catheter 4 bends, causing the first outer layer 40e to be pulled in the axial direction (in the distal direction and in the proximal direction). In addition, the engagement between the first inner layer protruding portion 12c and the first outer layer protruding portion 42c can reduce the probability that the first outer layer 40c will come off the inner layer 10c when the first outer layer 40c is pulled in the radial direction (outwardly).

The configuration of the reinforcing layer (braid) 35 of the catheter 4 may be modified in the following ways: (i) as in the catheter 2 shown in FIG. 4, an inward surface of the braid 35 as the reinforcing layer may be buried in the inner layer 10c and an outward surface of the braid 35 as the reinforcing layer may be buried in the first outer layer 40c; or (ii) as in the catheter 3 shown in FIG. 5, the braid 35 as the reinforcing layer may be disposed on the outer surface of the inner layer 10c.

Figure 8:
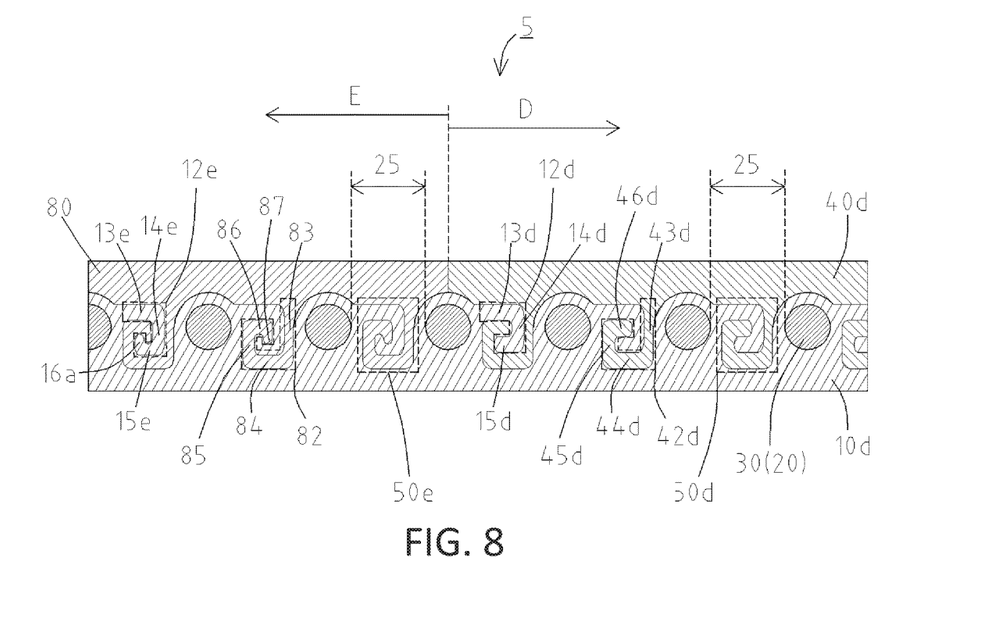
FIG. 8 is a partial sectional view of a catheter according to the disclosed embodiments, viewed in the same manner as in FIG. 3.

Next, referring to FIG. 8, a catheter 5 according to the disclosed embodiments is described below. Only differences from the catheter 1 shown in FIG. 3 will be described. A proximal side D of the catheter 5 comprises, in order from inside in the radial direction, a tubular inner layer 10d having the reinforcing layer (coil body) 30 disposed therein, and a first outer layer 40d covering the reinforcing layer (coil body) 30. A distal side E of the catheter 5 comprises, in order from inside in the radial direction, the tubular inner layer 10d having the reinforcing layer (coil body) 30 disposed therein, and a second outer layer 80 covering the reinforcing layer (coil body) 30.

The second outer layer 80 is made of a resin that is more flexible than the resin constituting the first outer layer 40d. The resin material constituting the second outer layer 80 is not particularly limited and may be a polyamide, a polyamide elastomer, a polyester, or a polyurethane, for example, as in the ease of the first outer layer 40d.

The proximal side D of the catheter 5 comprises, in the gap 25 of the reinforcing layer (coil body) 30, a first bonding portion 50d where a first inner layer protruding portion 12d of the inner layer 10d extends into the first outer layer 40d and is engaged with a first outer layer protruding portion 42d of the first outer layer 40d that extends into the inner layer 10d. The distal side E of the catheter 5 comprises, in the gap 25 of the reinforcing layer (coil body) 30, a second bonding portion 50e where a second inner layer protruding portion 12e of the inner layer 10d extends into the second outer layer 80 and is engaged with a second outer layer protruding portion 82 of the second outer layer 80 that extends into the inner layer 10d.

The first inner layer protruding portion 12d is composed of a proximally extending portion 13d, an inwardly extending portion 14d, and a distally extending portion 15d. The first outer layer protruding portion 42d is composed of an inwardly extending portion 43d, a distally extending portion 44d, an outwardly extending portion 45d, and a proximally extending portion 46d.

The second inner layer protruding portion 12e is composed of a proximally extending portion 13e, an inwardly extending portion 14e, a distally extending portion 15e, and an outwardly extending portion 16a. The second outer layer protruding portion 82 is composed of an inwardly extending portion 83, a distally extending portion 84, an outwardly extending portion 85, a proximally extending portion 86, and an inwardly extending portion 87.

In the catheter 5, the degree of engagement of the second bonding portion 50e is higher than the degree of engagement of the first bonding portion 50d (more specifically, the engaging force between the second inner layer protruding portion 12e and the second outer layer protruding portion 82 of the second bonding portion 50e is stronger than the engaging force between the first inner layer protruding portion 12d and the first outer layer protruding portion 42d of the first bonding portion 50d). When the catheter 5 is inserted into a peripheral section of a blood vessel, a bile duct, a pancreatic duct, or the like, the distal side E of the catheter 5 bends to a great extent to follow the curve of the vessel, and stress becomes concentrated at the second bonding portion 50e where the second outer layer 80 made of a flexible resin is bonded to the inner layer 10d. However, the high degree of engagement between the second inner layer protruding portion 12e and the second outer layer protruding portion 82 of the second bonding portion 50e (more specifically, the strong engaging force between the second inner layer protruding portion 12e and the second outer layer protruding portion 82), as well as the enlarged area across which the second outer layer 80 and the inner layer 10d are bonded to each other in the gap 25 of the reinforcing layer (coil body) 30, strengthen the bond between the second outer layer 80 and the inner layer 10d, which can reduce the probability that the second outer layer 80 made of a flexible resin will come off the inner layer 10d.

The configuration of the reinforcing layer (coil body) 30 of the catheter 5 may be modified in the following ways: (i) as in the catheter 2 shown in FIG. 4, an inward surface of the coil body 30 as the reinforcing layer may be buried in the inner layer 10d and an outward surface of the coil body 30 as the reinforcing layer may be buried in the first outer layer 40d and the second outer layer 80; or (ii) as in the catheter 3 shown in FIG. 5, the coil body 30 as the reinforcing layer may be disposed on the outer surface of the inner layer 10d. In the catheter 5, the reinforcing layer (coil body) 30 may be replaced by the reinforcing layer (braid) 35, as in the catheter 4 shown in FIG. 7.

Next, referring to FIG. 9 and FIG. 10, a balloon catheter 6 according to the disclosed embodiments is described below. FIG. 10 is an expanded view of part F shown in FIG. 9. The balloon catheter 6 is, for example, a therapeutic balloon catheter used for dilating a stenosis for curative purposes.

Figure 9:
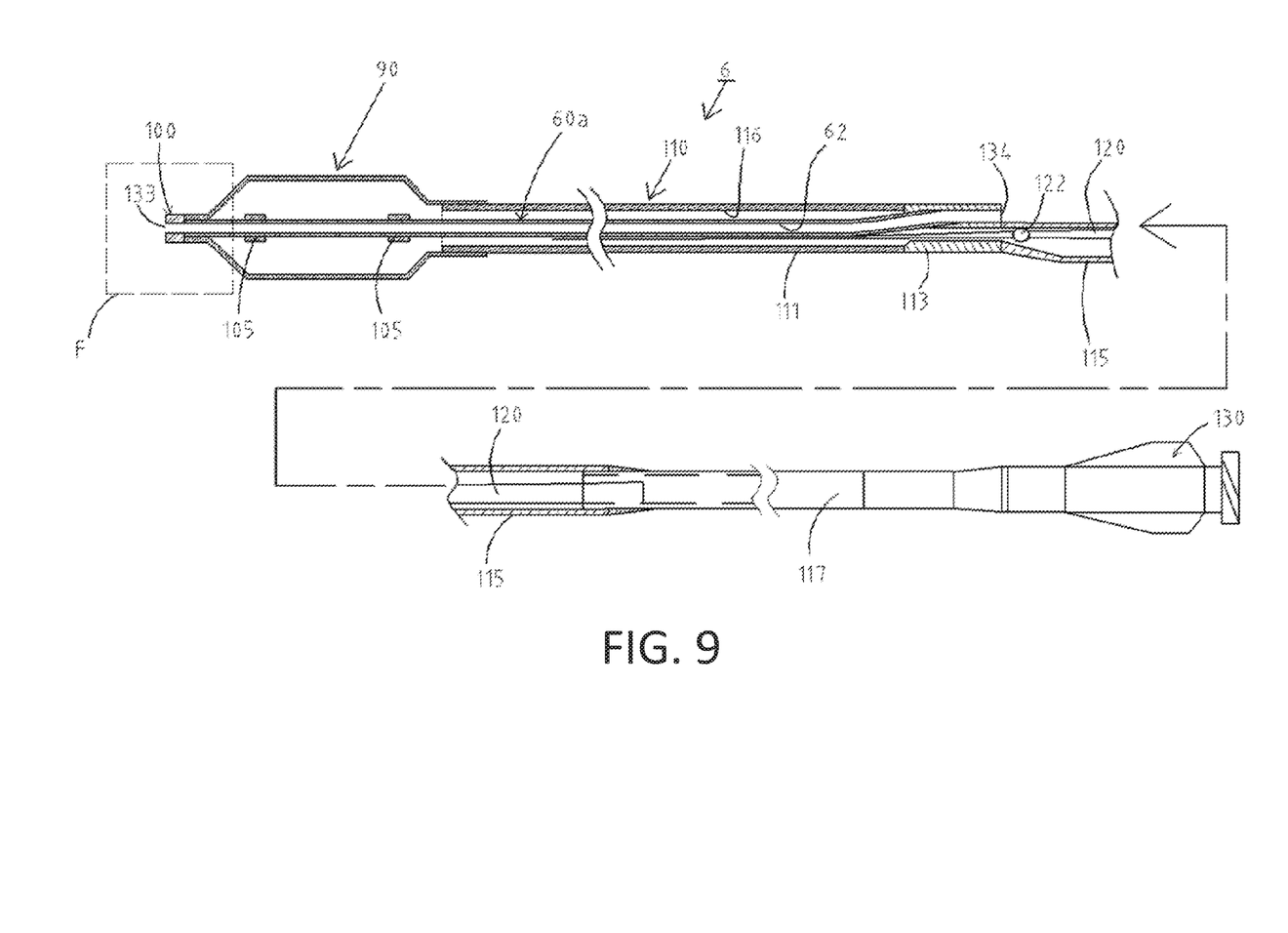
FIG. 9 is an overall view of a balloon catheter according to the disclosed embodiments.
Figure 10:
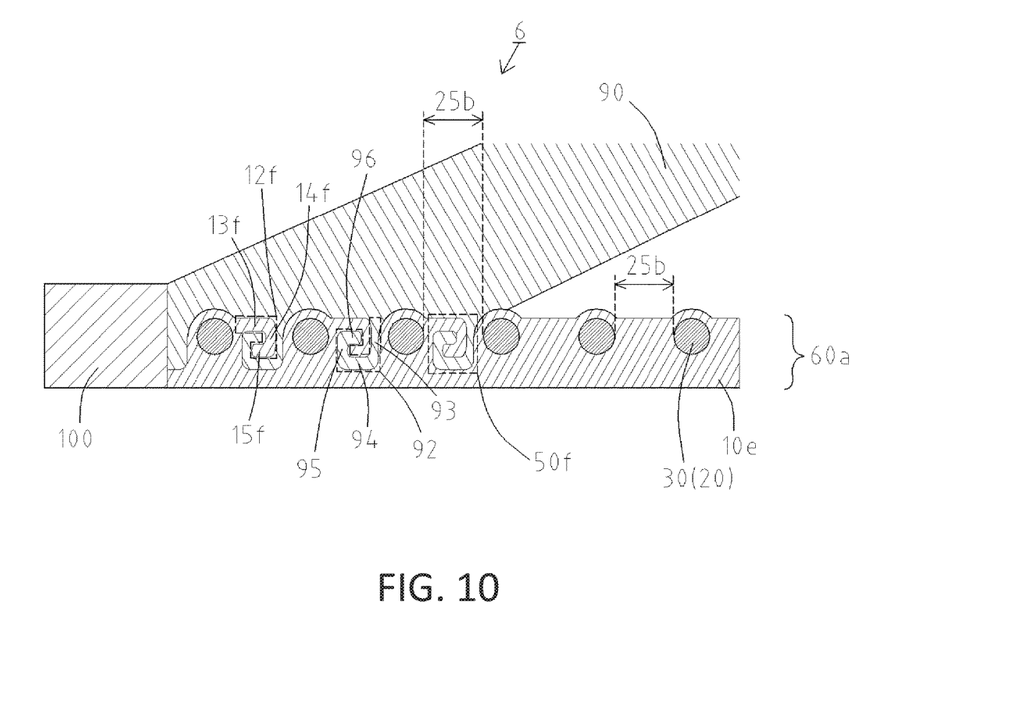
FIG. 10 is a partial expanded view of part F shown in FIG. 9, showing only the upper side of the catheter.

As shown in FIG. 9, the balloon catheter 6 comprises a balloon 90, a tip 100, an outer shaft 110, an inner shaft 60a, a reinforcing member 120, and a connector 130.

The balloon 90 for dilating a stenosis is made of a resin component. A distal end of the balloon 90 is bonded to a distal end of the inner shaft 60a and the tip 100. A proximal end of the balloon 90 is bonded a the distal end of the outer shaft 110.

The outer shaft 110 is a tubular component constituting an expandable lumen 116, which feeds liquid such as a contrast medium and physiological saline for expanding the balloon 90. The outer shaft 110 is composed of, from the distal end, an outer-shaft distal end 111, a guidewire port 113, an outer-shaft middle portion 115, and an outer-shaft proximal end 117. Each of the outer-shaft distal end 111 and the outer-shaft middle portion 115 is a tube made of a resin such as a polyamide, a polyamide elastomer, a polyolefin, a polyester, or a polyester elastomer. The guidewire port 113 is where the outer-shaft distal end 111, the outer-shaft middle portion 115, and the inner shaft 60a are bonded to each other.

The outer-shaft distal end 111 accommodates the inner shaft 60a inserted thereinto. Between the outer-shaft distal end 111 and the inner shaft 60a, the expandable lumen 116 described above is formed.

The outer-shaft proximal end 117 is a tubular metal component, called a hypotube. A distal end of the outer-shaft proximal end 117 is inserted into and bonded to a proximal end of the outer-shaft middle portion 115. A proximal end of the outer-shaft proximal end 117 has the connector 130 attached thereto. Liquid for expanding the balloon 90 such as a contrast medium and physiological saline can be fed from an indeflator (not shown) attachable to the connector 130, and travels through the expandable lumen 116 to reach and expand the balloon 90. The material constituting the outer-shaft proximal end 117 is not particularly limited and may be a super-elastic alloy such as stainless steel (SUS302, SUS304) or a Ni—Ti alloy.

Accommodated in the interior of the inner shaft 60a is a guidewire lumen 62 into which a guidewire is inserted. A proximal end of the inner shaft 60a is bonded to the guidewire port 113 of the outer shaft 110 to form a proximal end-side guidewire port 134. Through the proximal end-side guidewire port 134, a handler can replace a guidewire.

The tip 100 is bonded to the distal end of the inner shaft 60a and the distal end of the balloon 90. The tip 100 is made of a flexible resin. The material thereof is not particularly limited and may be a polyurethane or a polyurethane elastomer, for example. The tip 100 has a distal end-side guidewire port 133 on the distal end thereof.

The reinforcing member 120 is bonded to an inner circumference of a distal end of the outer-shaft proximal end 117. The reinforcing member 120 is a tapered metal wire that has a circular cross section tapered toward the distal end. The material of the reinforcing member 120 is not particularly limited and may be a super-elastic alloy such as stainless steel (SUS304) or a Ni—Ti alloy. The reinforcing member 120 extends through the outer-shaft middle portion 115 and then through the guidewire port 113 to reach the outer-shall distal end 111. The reinforcing member 120 has a pushing member 122 that can come into contact with the guidewire port 113.

The interior of the balloon 90 accommodates two markers 105 attached to an outer circumference of the inner shaft 60a. This configuration allows a handler such as a doctor to keep track of the exact location of the balloon 90 during coronary angiography, leading to reliable dilation of a stenosis.

As shown in FIG. 10, the inner shaft 60a comprises an inner layer 10e having the reinforcing layer (coil body) 30 disposed therein. The balloon 90 is bonded to the outer circumference of the inner shaft 60a and covers the reinforcing layer (coil body) 30.

In the portion where the inner shaft 60a is bonded to the balloon 90, a bonding portion 50f is disposed in the gap 25b of the reinforcing layer (coil body) 30. In the bonding portion 50f, an inner layer protruding portion 12f of the inner layer 10e extends into the balloon 90 and is engaged with a balloon protruding portion 92 of the balloon 90 that extends into the inner layer 10e.

The inner layer protruding portion 12f is composed of a proximally extending portion 13f, an inwardly extending portion 14f, and a distally extending portion 15f. The balloon protruding portion 92 is composed of an inwardly extending portion 93, a distally extending portion 94, an outwardly extending portion 95, and a proximally extending portion 96.

The bonding portion 50f enlarges the area across which the balloon 90 and the inner layer 10e are bonded to each other within the gap 25b of the reinforcing layer (coil body) 30, leading to a strengthened bond between the balloon 90 and the inner layer 10e. The balloon 90 is anchored in the reinforcing layer (coil body) 30, which reduces the probability that the balloon 90 will come off the inner layer 10e when the balloon catheter 6 bends, which causes the balloon 90 to be pulled in the axial direction (in the distal direction and in the proximal direction).

The engagement between the inner layer protruding portion 12f and the balloon protruding portion 92 of the bonding portion 50f can reduce the probability that the balloon 90 will come off the inner layer 10e when the balloon 90 is expanded radially (outwardly). In addition, the engagement between the inner layer protruding portion 12f and the balloon protruding portion 92 can allow a reduction in the thickness of the balloon 90 while maintaining the strength of the bond between the balloon 90 and the inner layer 10e, facilitating insertion of the balloon catheter 6 into a blood vessel, a bile duct, a pancreatic duct, or the like.

The inner shaft 60a of the balloon catheter 6 shown in FIG. 9 and FIG. 10 may be a combination of the inner layer 10, 10a, 10b, 10c, 10d of the catheter 1 to 5 and the reinforcing layer (coil body) 30 or the reinforcing layer (braid) 35 disposed in the inner layer 10, 10c, 10d or on the outer circumference of the inner layer 10a, 10b.

The first bonding portion 50, 50a, 50b, 50c, 50d of the catheter 1 to 5 may have any shape provided that the first inner layer protruding portion 12, 12a, 12b, 12c, 12d and the first outer layer protruding portion 42, 42a, 42b, 42c are engaged with each other therein. The second bonding portion 50e of the catheter 5 may also have any shape provided that the second inner layer protruding portion 12e and the second outer layer protruding portion 82 are engaged with each other therein. In addition, the bonding portion 50f of the balloon catheter 6 may also have any shape provided that the inner layer protruding portion 12f and the balloon protruding portion 92 are engaged with each other therein.

Figure 11:
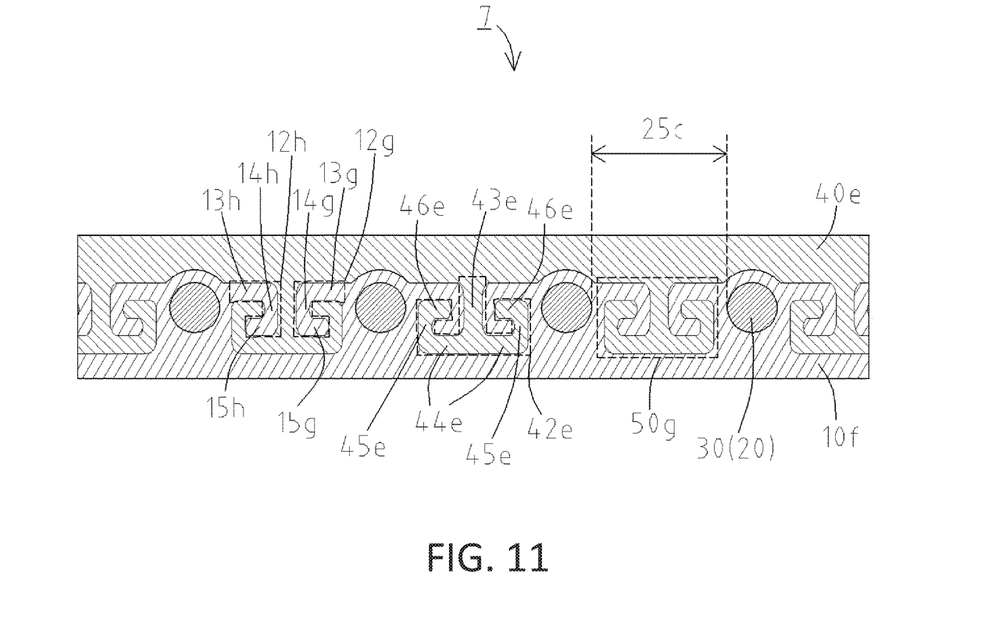
FIG. 11 is a partial sectional view of a catheter according to the disclosed embodiments, viewed in the same manner as in FIG. 3.

In a catheter 7 according to the disclosed embodiments, which is illustrated in FIG. 11, a first bonding portion 50g is disposed in a gap 25c of the reinforcing layer (coil body) 30. At the first bonding portion 50g, first inner layer protruding portions 12g, 12h of an inner layer 10f extend into a first outer layer 40e and are engaged with a first outer layer protruding portion 42e of the first outer layer 40e that extends into the inner layer 10f.

The first inner layer protruding portion 12g is composed of a distally extending portion 13g, an inwardly extending portion 14g, and a proximally extending portion 15g. The first inner layer protruding portion 12h is composed of a proximally extending portion 13h, an inwardly extending portion 14h, and a distally extending portion 15h. The first outer layer protruding portion 42e is composed of an inwardly extending portion 43c that bifurcates into an axially extending portion 44e that extends in both the distal direction and the proximal direction, two outwardly extending portions 45e extending outwardly from either end of the axially extending portion 44e (i.e., a proximal outwardly extending portion and a distal outwardly extending portion), and two terminal extending portions 46e extending distally from the proximal outwardly extending portion and proximally from the distal outwardly extending portion, respectively.

Figure 12:
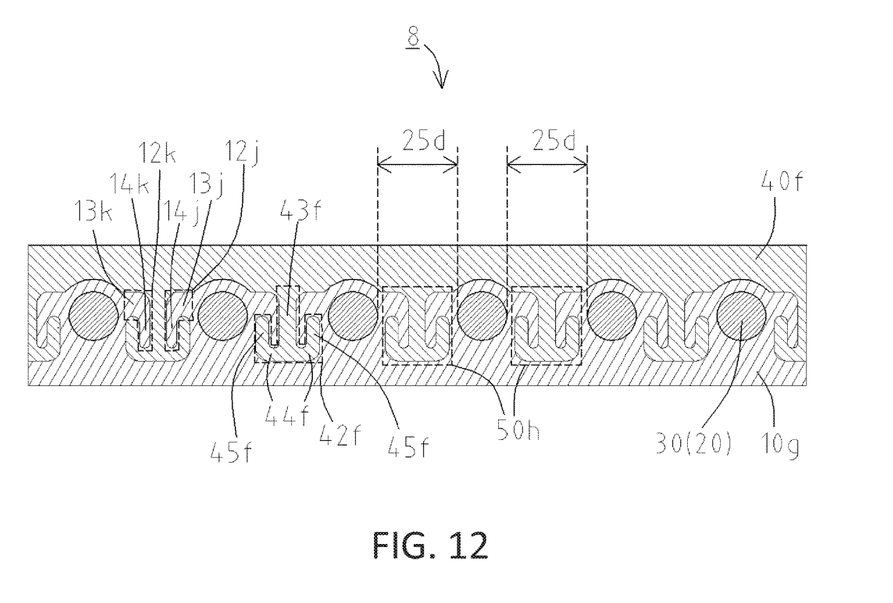
FIG. 12 is a partial sectional view of a catheter according to the disclosed embodiments, viewed in the same manner as in FIG. 3.

In a catheter 8 according to the disclosed embodiments, which is illustrated in FIG. 12 a first bonding portion 50h is disposed in a gap 25d in the reinforcing layer (coil body) 30. At the first bonding portion 50h, first inner layer protruding portions 12j, 12k of an inner layer 10g extend into a first outer layer 40f and are engaged with a first outer layer protruding portion 42f of the first outer layer 40f that extends into the inner layer 10g.

The first inner layer protruding portion 12j is composed of a distally extending portion 13j and an inwardly extending portion 14j. The first inner layer protruding portion 12k is composed of a proximally extending portion 13k and an inwardly extending portion 14k. The first outer layer protruding portion 42f is composed of an inwardly extending portion 43f that bifurcates into an axially extending portion 44f that extends in both the distal direction and the proximal direction, and two outwardly extending portions 45f extending outwardly from either end of the axially extending portion 44f (i.e., a proximal outwardly extending portion and a distal outwardly extending portion).

The reinforcing layer described above with respect to catheters 1 to 5, 7, and 8 and the balloon catheter 6 is either the coil body 30 or the braid 35, but the reinforcing layer is not limited to this configuration. For example, the reinforcing layer of any of the catheters 1 to 5, 7, and 8 and the balloon catheter 6 may be a hypotube (metal tube) having a helical slit serving as the gap.

What is claimed is:

1. A catheter comprising:
   a tubular inner layer;
   a reinforcing layer disposed at least partially within the tubular inner layer or on an outer circumference of the tubular inner layer, the reinforcing layer being made of wound wires, each adjacent pair of the wires having a gap therebetween; and
   a first outer layer covering the reinforcing layer,
   wherein a first bonding portion is disposed in the gap of the reinforcing layer, the first bonding portion including a first tubular inner layer protruding portion of the tubular inner layer that extends into the first outer layer and is engaged with a first outer layer protruding portion of the first outer layer that extends into the tubular inner layer.

2. The catheter according to claim 1, wherein:
   the first tubular inner layer protruding portion comprises a proximally extending portion, an inwardly extending portion, and a distally extending portion extending from the tubular inner layer in that order, and
   the first outer layer protruding portion comprises an inwardly extending portion, a distally extending portion, an outwardly extending portion, and a proximally extending portion extending from the first outer layer in that order.

3. The catheter according to claim 2, wherein the first tubular inner layer protruding portion further comprises an outwardly extending portion that terminates at the proximally extending portion of the first tubular inner layer protruding portion.

4. The catheter according to claim 1, wherein the first bonding portion includes at least two first tubular inner layer protruding portions that extend into the first outer layer and are engaged with the first outer layer protruding portion.

5. The catheter according to claim 4, wherein the first outer layer protruding portion is bifurcated and includes two outwardly extending portions that engage with the two first tubular inner layer protruding portions.

6. The catheter according to claim 1, further comprising:
   a second outer layer covering an outer circumference of the reinforcing layer and arranged distal to the first outer layer, the second outer layer being made of a material that is more flexible than a material of which the first outer layer is made,
   wherein:
   a second bonding portion is disposed in the gap of the reinforcing layer, the second bonding portion having a second tubular inner layer protruding portion of the tubular inner layer that extends into the second outer layer and is engaged with a second outer layer protruding portion of the second outer layer that extends into the tubular inner layer, and
   a degree of engagement of the second bonding portion is higher than a degree of engagement of the first bonding portion.

* * * * *